United States Patent [19]

Sugiura et al.

[11] 4,277,514

[45] Jul. 7, 1981

[54] FORGERY RESISTANT DOCUMENT WITH COLORED AREAS AND METHOD FOR THWARTING REPRODUCTION OF SAME

[75] Inventors: Takeo Sugiura, Tokorozawa; Keiji Miyajima, Chiba; Hideo Nagatomo; Kiyoshi Masui, both of Saitama, all of Japan

[73] Assignee: Toppan Printing Co., Ltd., Japan

[21] Appl. No.: 16,721

[22] Filed: Mar. 2, 1979

[30] Foreign Application Priority Data

Mar. 7, 1978 [JP] Japan .................................. 53-25662
Dec. 18, 1978 [JP] Japan ................................ 53-158227

[51] Int. Cl.[3] ................................................ A61B 5/10
[52] U.S. Cl. ........................................ 427/1; 283/8 R
[58] Field of Search ............................ 427/7; 283/8 R

[56] References Cited

U.S. PATENT DOCUMENTS

| | | | |
|---|---|---|---|
| 1,002,600 | 9/1911 | Bawtree et al. | 427/7 |
| 1,692,405 | 11/1928 | Freeman | 427/7 |
| 3,679,448 | 7/1972 | Tramposch | 427/7 |
| 3,679,449 | 7/1972 | Nagot et al. | 427/7 |
| 3,713,861 | 1/1973 | Sharp | 427/7 |
| 3,852,088 | 12/1974 | Godlewski et al. | 427/7 |
| 4,066,280 | 1/1978 | La Capria | 427/7 |

*Primary Examiner*—Ralph S. Kendall
*Assistant Examiner*—Janyce A. Bell
*Attorney, Agent, or Firm*—McGlew and Tuttle

[57] ABSTRACT

A document with a color pattern which is resistant to forgery by photo reproducing process, at least a portion of the color pattern comprising, a coloring material having a spectral reflection factor curve which is relatively high at a wavelength in at least one of the areas below 450 nm and about 650 nm, with respect to the rest of the curve. A method is also disclosed for avoiding reproduction of a document having colored areas using photo reproducing processes.

7 Claims, 6 Drawing Figures

FORGERY RESISTANT DOCUMENT WITH COLORED AREAS AND METHOD FOR THWARTING REPRODUCTION OF SAME

BACKGROUND OF THE INVENTION

1. Field of the Invention

This invention relates in general, to a document with a pattern or an object representing colored patterns thereon which is difficult to make reproductions of, and more specifically, to patterns made with some specific kinds of coloring matter, which, when reproducted using processes which utilize photosensitive emulsion, including color photography and color copying process, reproductions in a color entirely different from that of the original. Such documents or objects can be utilized as an object whose reproduction is undesirable such as paper money, various kinds of securities and the like, resultantly preventing forgery of such articles of value.

2. Description of the Prior Art

The recently developed technology for reproduction of colored pattern which utilizes sensitive emulsion, such as color photography and the color reproduction process by means of color copyers, is able to reproduce patterns in a color which can be practically recognized to be identical to that of the original. A potential application of this convenient technology to colored objects whose reproduction is undesirable may cause social problems possibly even criminal acts. Particularly when it is utilized for reproduction of paper money, stock-certificates, bond certificates, atamps, checks, drafts, bills of lading, letters of guarantee, credit cards, various certificates, various coupons, various slips, and/or the objects with such nature, and if the reproductions of such objects should circulate in the market place or through various transactions, it would evidently cause disturbances for economic and financial activities, and it would be serious enough not to allow oversight thereof from the viewpoint of maintaining social justice.

Included in the means available in the prior art and which are applicable for prevention of forgery of such objects of value are:

(1) Employment of particular kinds of paper such as the paper having watermarks therein, (2) Utilization of particular patterns such as fine, minute and/or complicated background camouflages or ground designs and hidden marks, (3) Utilization of a particular process for representation of patterns such as mandatory employment of particular and sophisticated graving machines for production of plates, (4) Employment of a particular, sophisticated and expensive printing process such as Sammel druck machines. Each of these means is inevitably accompanied by costwise disadvantage. In addition, the recent development in the aforementioned technology for reproduction of colored patterns to be made by utilizing photosensitive emulsion which is excellent in performance and simple in handling operation, has added another disadvantage to these conventional means for prevention of reproduction of objects representing colored patterns thereon. When a colored object, hereinafter refered to as a document, is reproduced either directly with such color reproduction technology or indirectly with such technology which is utilized for production of blocks or plates with which printing will be made, some magnitude of discrepancy would be recognized between an original and reproduction from the viewpoint of visibility, dimensional distortion of patterns and/or paper quality. However, it is not seldom that even experts have a difficult time identifying a colored object as a reproduction. Particularly, in view of the fact that the ordinary transactions are carried out by personnel which is nonprofessional in the technical field without using time for making sure of the validity of the paper money, the securities and/or the documents to be transferred by some means including direct comparison with the genuine piece, it would be unrealistic to assume that the aforementioned color reproduction technology will not be applied to the undesirable purposes of forgery.

As a result, it is a social demands to provide a document with colored patterns that can be used as valuable documents, which is difficult to make a reproduction of by means of a process for reproduction of colored patterns to be made by utilizing photosensitive emulsion.

SUMMARY OF THE INVENTION

An object of this invention is to provide an object representing colored patterns thereon or document with pattern which does not allow the technology for reproduction of colored patterns by utilizing photosensitive emulsion, to be used to produce reproductions in a color, acculately resembling that of the original patterns.

Another object of this invention is to provide an object representing colored patterns thereon which is difficult to make reproductions of, the object being reproducable without utilizing any particular plates for printing or any particular printing process.

A further object of this invention is to provide an object representing colored patterns thereon and whose reproduction by means of the process for reproduction of colored patterns by utilizing photosensitive emulsion, can be readily identified as a reproduction by nonprofessional personnel including the individual who made the reproduction, resultantly causing an effect to discourage a potential forger from trying to circulate the forgery in the market place or through other transactions and further causing an effect to prevent forgery of an object whose reproduction is undesirable by means of such technology.

An additional object of this invention is to provide an object representing colored patterns thereon and whose reproduction produced by means of the process for reproduction of colored patterns to be made by utilizing photosensitive emulsion can be identified as a reproduction by the public, resulting in an effect that a potential forgery is prevented from circulating the reproduction.

A further object of this invention is to provide an object representing colored patterns thereon and which can be utilized as an object of value, the object being difficult to reproduce by means of technology utilizing photosensitive emulsion, resulting in an effect to provide an object of value which is difficult to make forgeries of and whose production requires no particular technology, ultimately resulting in an effect to reduce the cost for prevention of such forgery of such articles of value or to increase the effect for prevention of forgery of such articles of value without requiring additional cost.

B. A still further object of the present invention is to provide a document with the colored pattern which is resistant to color accurate reproduction by photo reproducing processes, at least a portion of the color pattern comprising, a coloring matter having a spectral reflection factor curve which is relatively high at a wavelength in at least one of the areas below 450 nm and above 650 nm, with respect to the rest of the curve.

A still further object of the present invention is to provide a method for resisting forgery of a document having a colored pattern thereon comprising forming at least a portion of the colored pattern on the document of a coloring material having a spectrum reflection factor curve which is high at the wave length of below 450 nm and or above 650 nm whereby reproduction of the document using photosensitive emulsions will result in a reproduction having colors different from that of the original.

Other objects, features and advantages of this invention will be pointed out in, or be apparent from the following description and claims and illustrated in the accompanying drawings, which disclose the principles of this invention and the best mode which has been contemplated of applying those principles.

Other objects, features and advantages of this invention will be pointed out in, or be apparent from, the following description and claims and illustrated in the accompanying drawings, which disclose the principles of this invention and the best mode which has been contemplated of applying those priciples.

DESCRIPTION OF THE PREFERRED EMBODIMENT

Silver halogenide, zinc oxife, cadmium sulfide, and the like, are presently utilized as the photosensitive emulsions employed for the reproduction of colored patterns in color photography and in color copyers. Of these photosensitive emulsions, silver halogenides generally show the spectral characteristics as illustrated in FIGS. 1 and 2.

Figure 1:
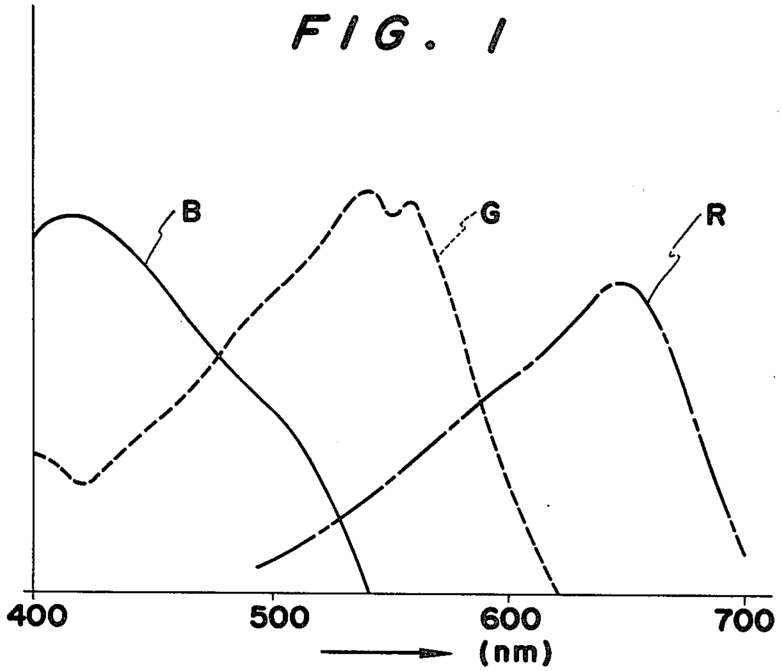
FIG. 1 is a diagram showing the spectral sensitivity of each photosensitive layer of the silver halogenide photosensitive emulsions respectively sensitive to three kinds of elementary color, blueviolet, green and red.

FIG. 1 is a diagram showing the spectral sensitivity of each photosensitive layer of the silver halogenide photosensitive emulsions respectively sensitive to three kinds of elementary color; blueviolet, (curve B) green (curve G) and red (curve R). While a photosensitive layer that is sensitive to blueviolet is expected to have a uniform sensitivity to the wavelength of light covering 400 nm through 500 nm, it actually has an irregular sensitivity in the wavelength range from slightly longer than 400 nm through considerably longer than 500 nm. While another photosensitive layer to be sensitive to green is expected to have a uniform wavelength covering 500 nm through 600 nm, it actually has an irregular sensitivity having double peaks around the middle of the wavelength range covering considerably shorter than 500 nm through considerably longer than 600 nm. While the third photosensitive layer to be sensitive to red is expected to have a uniform sensitivity to the wavelength range covering 600 nm through 700 nm, it actually has an irregular sensitivity having a peak in the middle of the wavelength range between 600 nm and 700 nm and covering a wide wavelength range from slightly longer than 500 nm through approximately 700 nm.

Figure 2:
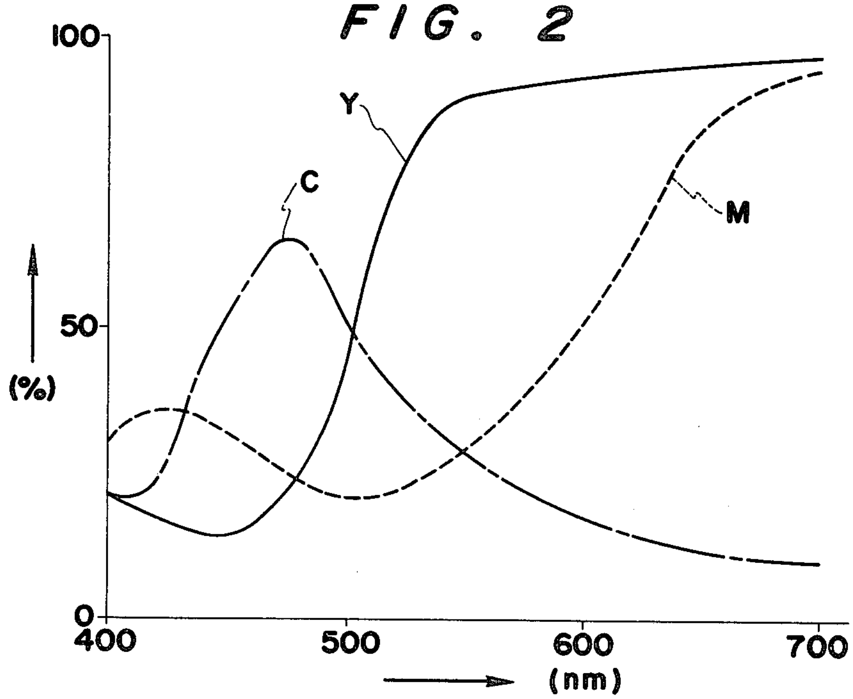
FIG. 2 is a diagram showing the spectral reflection factor of three kinds of presently available silver halogenide-based coloring matter each of which respectively develops colors, cyan, magenta and yellow on a color photograph.

FIG. 2 is a diagram showing the spectral reflection factor of three kinds of presently available silver halogenide-based coloring matter each of which respectively develops three independent colors; cyan (curve C), magenta (curve M) and yellow (curve Y) on a color photograph. Each of these colors is developed in each color developing layer of a color photograph, keeping some quantitative relations with the magnitude of exposure of each of the aforementioned photosensitive layers, based on the principle defined in the subtractive color mixing process. It is well known that the three colors of the coloring matter are respectively complementary colors of the three elementary colors. The following as noted in FIG. 2: (1) While yellow is expected to uniformly cover the wavelength range of 500 nm–700 nm, the actual reflection factor extends to the wavelength range of 400 nm–500 nm. (2) While magenta is expected to uniformly cover the two independent wavelength ranges of 400–500 nm and 600–700 nm, it actually does not show the expected magnitude of reflection factor in the wavelength range of 400–500 nm. (3) While cyan is expected to uniformly cover the wavelength range of 400–600 nm, it has a triangle peak around the wavelength range slightly shorter than 500 nm, although it scarcely covers the entire expected wavelength range.

In accordance with the subtractive color mixing process which is used in the technology for reproducing colored patterns to be made by utilizing photosensitive emulsion, the photosensitive layer exposed to blueviolet is developed by superposition of cyan and magenta, the layer exposed to green is developed by superposition of cyan and yellow, and the layer exposed to red is developed by superposition of magenta and yellow.

Figure 3:
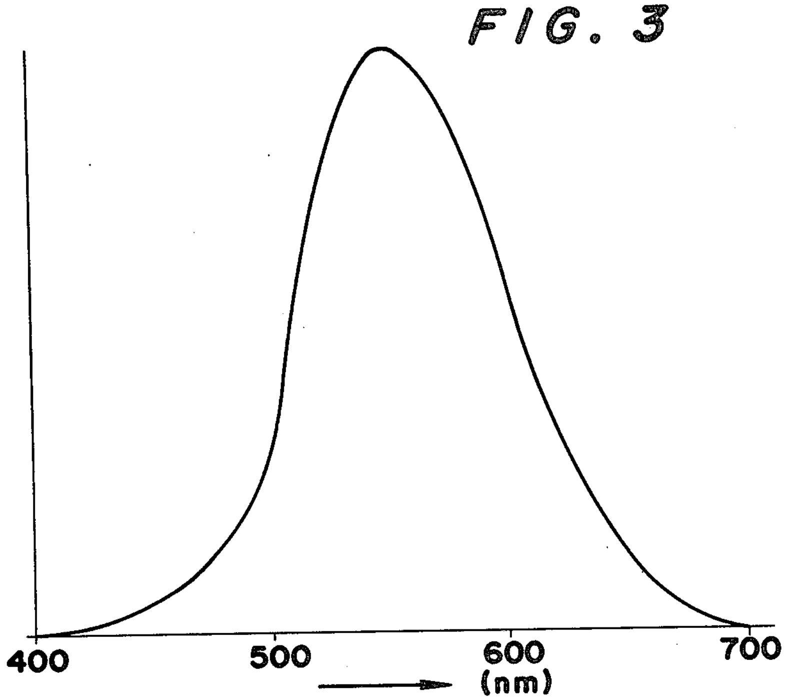
FIG. 3 is the human relative luminosity curve.

FIG. 3 is the human relative luminosity curve. Referring to the figure, the magnitude of the human sense of sight varies depending on the wavelength of light to be seen and has a wide dispersion, ranging from 450 nm to 650 nm and centering around 550 nm. A certain intensity of light thus gives the human sense of sight a different magnitude of impression, depending on the range of wavelength of the light. Light with a wavelength close to 550 nm is thus sensed more strongly than light with a wavelength close to 400–450 nm or 650–700 nm. Also it is seen that the human sense of sight is marginal in the wavelength ranges of 400–450 nm and 650–700 nm.

Supposing a pattern is represented with a kind of coloring matter whose spectral reflection is limited to the wavelength range close to 700 nm, it can scarcely be seen by humans, because the reflection of such coloring matter can not stimulate the human sense of sight. However, if the photosensitive emulsions having the sensitivity as shown in FIG. 1 are employed, when the subtractive color mixing process is applied to reproduction of a pattern represented with the aforementioned kind of coloring matter, the reproduction will be represented by superposition of yellow and magenta both of which will be developed with the same magnitude. Therefore, the reproduction will have a spectral reflection factor diagram having a shape in which a large and flat peak is observed in the wavelength range of 600–700 nm on top of another flat zone observed in the wavelength range of 500–600 nm. Since the human relative luminosity curve shows marginal sensitivity in the wavelength range beyond 650 nm, the human sense of sight will be more stimulated by the wavelength range of 600–650 nm. This means the reproduction is seen in red. Here, it is noted that all the monochromatic lights recognized within the wavelength range of 600–700 nm are represented as a compound light having the wavelength range entirely covering 600–700 nm. This color changing phenomenon is true also for the blueviolet range with the wavelength range of 400–500 nm and for the green range with the wavelength range of 500–600 nm.

This color changing effect is caused since (1) the spectral reflection characteristic of a reproduction, produced by the color reproduction process utilizing photosensitive emulsion, is considerbly different from that of the original color, and since (2) that this change in spectral reflection characteristic is caused to give much more influence to the human sense of sight due to the nonlinear characteristic thereof. Therefore, this color changing effect is defined as an effect to change color caused by (1) the change in the spectral reflection characteristic for a reproduction of a specific kind of coloring matter having a strong spectral reflection factor in the wavelength range in which the magnitude of the human spectral luminous efficacy is marginal, which is produced by the color reproduction process utilizing photosensitive emulsion having spectral sensitivity in at least one of the wavelength ranges consisting of the human visible range and the adjacent wavelength ranges, and by (2) magnification of the effect to the human sense of sight, because the change takes place in the wavelength range of 400–500 nm or 600–700 nm in which the human relative luminosity curve shows a sharp rise from zero.

Figure 4:
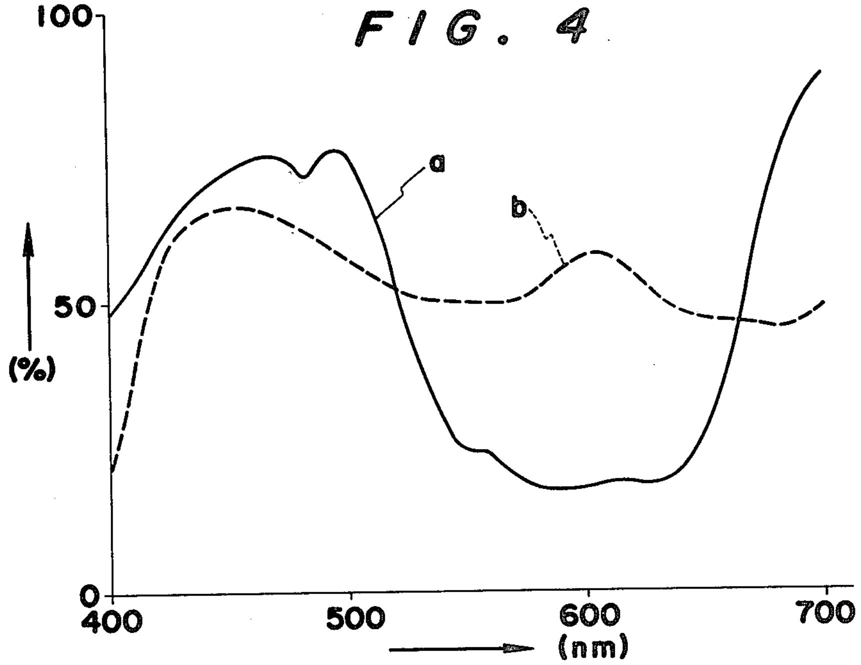
FIG. 4 is a diagram showing the spectral sensitivity of cobalt blue and the reproduction thereof by means of the color copying process.

A preferable example of the color changing effect will be described below. Referring to FIG. 4 which shows the spectral reflection factor diagram of cobalt blue (hereinafter referred to as (*4a*)) and the spectral reflection factor diagram of the reproduction of the same (hereinafter referred to as (*4b*)) produced by means of a Fuji CB color copyer, model CB 430, produced by Fuji Photografic Film Co. of Japan. In the figure, the curve (a) represents the spectral reflection factor diagram of the coloring matter (*4a*) and the curve (b) represents that of the coloring matter (*4b*). Though curve (a) shows a sharply raised and strong spectral reflection factor range in the wavelength range beyond 650 nm, since the magnitude of the human spectral luminous efficacy is marginal in the wavelength range, the human sense of sight is stimulated only by the other strong spectral reflection factor range in the wavelength range of 400–500 nm, particularly by the wavelength range of 450–500 nm in which the human sense of sight has a rather strong sensitivity. As a result, coloring matter (*4a*) is seen as blue. However, curve (b) shows a considerably different characteristic, in which the spectral reflection factor in the wavelength ranges of 400–500 nm and 650–700 nm was reduced and the spectral reflection factor in the wavelength range of 550–650 nm was increased. Therefore, coloring matter (*4b*) was changed the color and it is not be seen as blue. As a result, an object colored with a kind of coloring matter having this color changing effect does not allow the color reproduction processes to be made by utilizing photosensitive emulsion to produce a reproduction having a color similar to that of the original.

Figure 5:
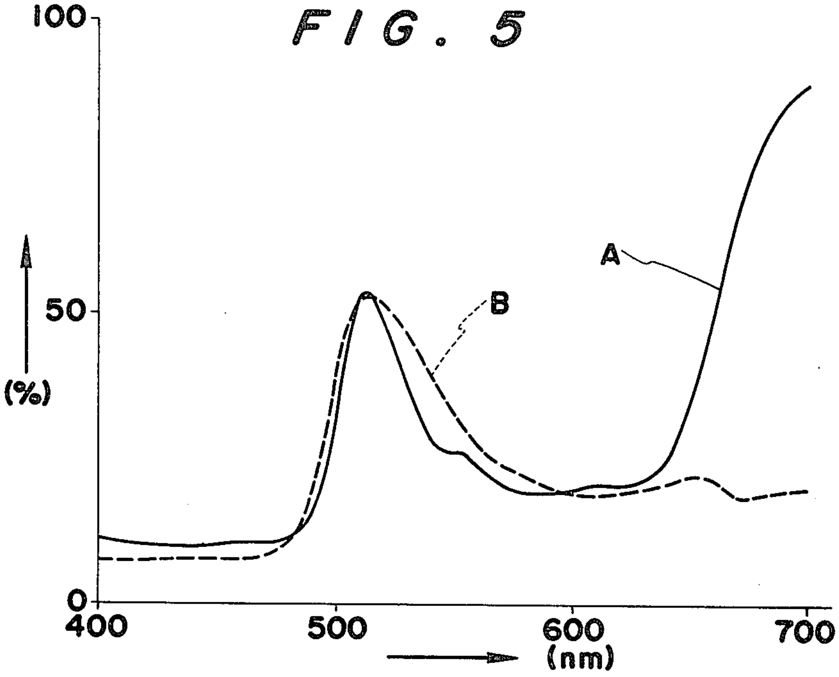
FIG. 5 is a diagram comparing the spectral reflection factors of a kind of coloring matter produced by kneading one part of cobalt blue with one part of disazo compound yellow and of chromium oxide.

The principle of this color changing effect will be described below, referring to a more preferable example. FIG. 5 compares the spectral reflection factors of a kind of coloring matter, produced by kneading one part of cobalt blue with one part of disazo compound yellow (hereinafter referred to as (A)), and of chromium oxide (hereinafter referred to as (B)). Within the wavelength range of 400–650 nm, both kinds of coloring matter show the same tendency in the spectral reflection characteristics. However, in the wavelength range beyond 650 nm, coloring matter (A) has a sharply raised strong spectral reflection factor range. Despite this, coloring matter (B) has a rather weak spectral reflection factor range. Since the magnitude of the human spectral luminous efficacy is marginal in the wavelength range in which the difference is observed for the spectral reflection characteristics, the human sense of sight can not distinguish one of these kinds of coloring matter from the other. As a result, when exposed to white light, the combined kinds of coloring matter (A) produce reflections similar to that of coloring matter matter (B), and both of them are seen as blue green. The reproductions of these kinds of coloring matter (A) and (B), however produced by means of a Fuji CB color copyer, model CB 430, give the spectral reflection factor diagram shown in FIG. 6. The figure is interpreted as follows. As to curve A', (1) the sharply raised strong spectral reflection factor range disappeared from below the wavelength range close to 512 nm and beyond 660 nm, (2) a strong spectral reflection factor range appeared in the wavelength range of 600–700 nm, (3) the magnitude of the spectral reflection factor increased in the wave length-range of 500–600 nm and (4) the variation in the magnitude of spectral reflection factor was moderated. On the other hand, as to curve B', no difference is observed from curve A' in the wavelength range of 400–530 nm, (2) no notable change was made for the wavelength range of 600–700 nm. As a result, the effect of the color reproduction process toward coloring matter (B) is not substantial and is limited to the chroma, causing no change in color. However, the effect of the same color reproduction process toward coloring matter (A) is considerably large, resulting in a change in color from blue to yellow brown or dark red.

Based on the principle of the subtractive color mixing process, the reasons why the same process caused different effects depending on the kinds of coloring matter applied thereto are considered as follows. (1) Although a spectral reflection factor range which is sharp is rise, high in value and wide in the width of the wavelength range exists in the less visible wavelength range beyond 650 nm, the human sense of sight can not recognize the reflection from this wavelength range. (2) The colors of both coloring matters (A) and (B) are determined by the reflection from the wavelength range close to 512 nm, and both are seen as the same color. (3) Due to the effects caused by the subtractive color mixing process, the reproduction of coloring matter (A) gained a strong and broad spectral reflection range in the wavelength range of 600–700 nm. (4) Out of the wavelength range of 600–700 nm, the wavelength range of 600–650 nm in which the magnitude of the human spectral luminous efficacy is large determined the color of the reproduction.

Gray is also considered to have a considerable magnitude of the color changing effect. In other words, when a spectral reflection factor diagram shows a flat curve along the entire wavelength range, excepting the wavelength range in which the human spectral luminous efficacy is marginal, the corresponding coloring matter is seen as gray. However, if the spectral reflection factor diagram shows a notable spectral reflection factor in at least one of the wavelength ranges of 650–700 nm and 400–450 nm, the reproduction of the coloring matter made by utilizing photosensitive emulsion is seen in red or in blue.

Three independent groups of coloring matter are included in the coloring matter having the color changing effect to which this invention is directed. The required characteristic of the first group is that: (1) a notable spectral reflection range exists in the wavelength range of 400–450 nm preferably 420–450 nm and/or 650–700 nm preferably 650–680 nm, (2) the notable spectral reflection range supplies sufficient quantity of light to the photosensitive materials employed for the color reproduction process, (3) the magnitude of the notable spectral reflection facter is large and the difference between the magnitude and that of the wavelength slightly longer than 450 nm or slightly shorter than 650 nm is 30% or more, preferably 40% or more, and (4) the value of the spectral reflection factor at the wavelength slightly longer than 450 nm or slightly shorter than 650 nm is 40% or less, preferably 30% or less. The required characteristic of the second group is that, in addition to the three items specified for the first group, the value of the spectral reflection factor is approximately uniform for the entire wavelength range, excepting the wavelength range shorter than 450 nm or longer than 650 nm. This means the coloring matter is seen in gray by men. The required characteristic of the third group is that, in addition to the three items specified for the first group, the coloring matter has one or more sharply risen highly peaked spectral reflection range to determine the color of the coloring matter at some wavelength range within the wavelength range of 450–650 nm. This means the color of such coloring matter is either blue, green, violet, or some others.

Included in coloring matter having the color changing effect to which this invention is directed are some kinds of the inorganic pigment, some kinds of dye for cotton and some kinds of dye for polyester. More specicically, in addition to the coloring matter produced by kneading disazo compound yellow and cobalt blue referred to in the above, included are cobalt blue light, cobalt blue deep, deep cobalt violet, peacock blue A, carbazole violet, chromophthal violet B (Ciba Geigy make), et al.

Completely no restrictions are imposed for the process to represent colored patterns on an object to implement this invention. In other words, any process for representation of colored patterns is acceptable. In addition to hand writing, any type of color representation process including letter press printing process, lithographic printing process, intaglio printing process, and the like is acceptable. Further, no restrictions are imposed for the document or quality of the object to be represented by the colored patterns. In other words, any kind of object is acceptable, including paper, metal, wood, cloth, synthetic resin, and the like, and all are termed a document for convenience.

Figure 6:
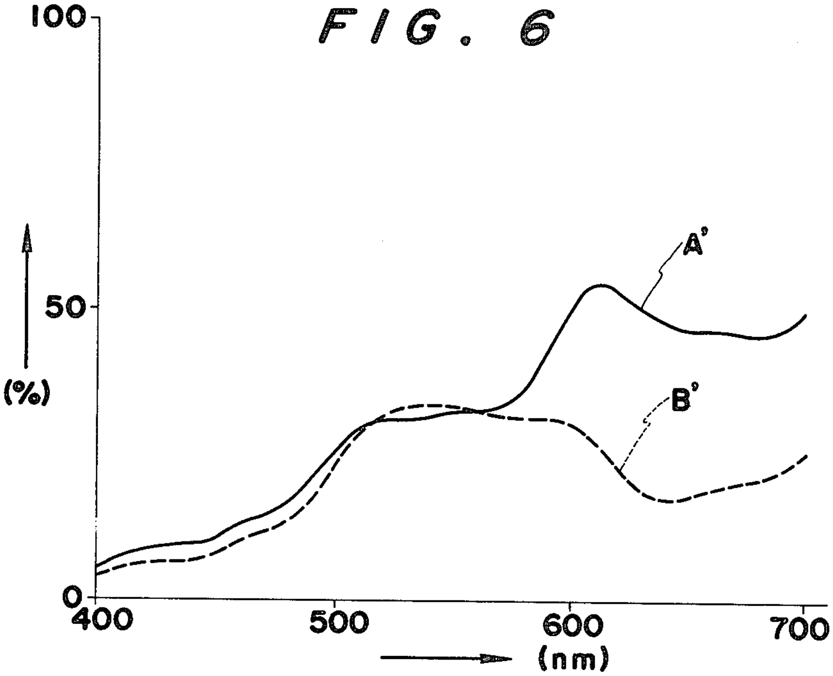
FIG. 6 is a diagram comparing the spectral reflection factor of the reproductions, produced by means of a Fuji CB color copyer, model CB 430, of a kind of coloring matter produced by kneading one part of cobalt blue to one part of disazo compound yellow and of chromium oxide.

When two kinds of coloring matter, referred to in the explanation made referring to FIGS. 5 and 6, are used for production of a hidden mark, a remarkable effect can be expected for prevention of forgery. In other words, when a pattern represented with a kind of coloring matter having the color changing effect is surrounded by the other kind of coloring matter which is seen in the same color as the above and which does not have the color changing effect, the pattern becomes visible on a reproduction made by utilizing photosensitive emulsions, though it can not be distinguished from the surrounding background on the original. In this case, when the difference in the magnitude of the reflection factor between the pattern and the background is 30% or more, preferably 40% more, on the reproduction, a notable effect can be expected.

A prefered embodiment and example of the invention is shown below: A pattern reading "This is a copy" was placed on a piece of fine quality paper with a kind of coloring matter which is a mixed composite containing one part of cobalt blue and one part of disazo compound yellow and which has a spectral reflection characteristic shown in FIG. 5(A). The space surrounding the above pattern was filled with another kind of coloring matter which is a mixture composite containing chromium oxide and which has a reflection factor characteristic shown in FIG. 5(B). Though the human sense of sight can not distinguish the pattern from the background, the photograph taken with KODAK EKTACHROME 64 Professional Film made by Eastman Kodak Co. of the U.S.A. presented the pattern reading "This is a copy" in red green on the background in green. A reproduction of the same by means of a Fuji CB color copyer made by Fuji Photographic Film Co. of Japan also presented a similar pattern. The reflection factors of the coloring matter (A) in the wavelengths of 650 nm, 680 nm and 700 nm are, respectively, 30%, 80% and 90%. The reflection factors of the coloring matter (B) in the wavelengths of 650 nm, 680 nm and 700 nm are, respectively, 22%, 20% and 19%.

In conclusion, according to this invention, disadvantages pointed out above involved with the prior art, are removed. An object representing patterns thereon in accordance with this invention does not allow the color reproduction process to be made by utilizing photosensitive emulsion to make reproduction thereof in a color accurately resembling to that of the original. The object is thus possibly utilized as an object whose reproduction is undesirable. An object representing patterns thereon in accordance with this invention allows non-professional personnel to distinguish a reproduction produced by utilizing photosensitive emulsion, from the original resulting in an effect to discourage a potential forger an try to circulate the forgery in the market place and in another effect not to allow the forgery to circulate in the market place. An object representing patterns thereon in accordance with this invention is possible to be produced without using any particular plates or blocks for printing purpose or any particular printing process, resulting in a reduction of cost for prevention of forgery of articles whose reproduction is undesirable.

What is claimed is:

1. An object with a colored surface pattern provided with a material containing at least one kind of coloring matter having a spectral reflection factor characteristic which exhibits a high spectral reflection factor in at least one of the wavelength ranges below 450 nm and above 650 nm, whereby reproduction of said colored surface pattern by means of any of a photo-color-copier and color photography utilizing photosensitive materials having spectral sensitivity in at least one of the wavelength ranges consisting of the human visible range and the adjacent wavelength ranges thereto is avoided, said coloring matter also having at least one high spectral reflection factor characteristic within the range between 450 nm and 650 nm so that a human viewer sees a color of said matter different from the color reproduced.

2. A document according to claim 1 wherein at least some spectral reflection factors are located in the wavelength range between 450 nm and 650 nm and a relatively high spectral reflection factor is located at a wavelength range in at least one of the ranges between about 420 to 450 nm and 650 to 680 nm so that the pattern appears to be one color to viewer and is reproduced in another color by the photoreproduction process.

3. A document according to claim 1 wherein said coloring matter is selected from the group of coloring materials consisting of cobalt blue light, cobalt blue deep, deep cobalt violet, peacock blue A, carbazole violet, chromophthal violet B, and a material produced by kneading disazo compound yellow and cobalt blue.

4. A document according to claim 1 wherein the spectral reflection factor curve is relatively high at a wavelength of between about 400 to 450 nm.

5. A document according to claim 1 wherein the spectral reflection factor curve is relatively high at a wavelength of between about 650 to 700 nm.

6. A document according to claim 1 wherein the spectral reflection factor curve in the area between 450 to 650 nm is at least 40%.

7. A document according to claim 1 wherein the spectral reflection factor curve is approximately uniform in the area between 450 to 650 nm.

* * * * *